United States Patent [19]

Kunishige et al.

[11] Patent Number: 4,474,882

[45] Date of Patent: Oct. 2, 1984

[54] MICROBIOLOGICAL PROCESS FOR THE PREPARATION OF UNSATURATED DICARBOXYLIC ACIDS

[75] Inventors: Etsumi Kunishige; Tsuyoshi Morinaga, both of Saitama, Japan

[73] Assignee: Daicel Chemical Industries, Ltd., Osaka, Japan

[21] Appl. No.: 304,284

[22] Filed: Sep. 21, 1981

[30] Foreign Application Priority Data

Oct. 9, 1980 [JP] Japan ................... 55-141431

[51] Int. Cl.$^3$ ............ C12P 7/44; C12P 7/64; C12R 1/74
[52] U.S. Cl. ..................... 435/142; 435/134; 435/924
[58] Field of Search ......... 435/134, 135, 142, 145, 435/924

[56] References Cited

U.S. PATENT DOCUMENTS

| 3,409,506 | 11/1968 | Stevens et al. | 435/134 |
| 3,483,083 | 12/1969 | Elson et al. | 435/142 |
| 3,843,466 | 10/1974 | Akabori et al. | 435/924 |
| 3,912,586 | 10/1975 | Kaneyuki et al. | 435/142 |
| 3,975,234 | 8/1976 | Hitzman | 435/142 |
| 4,220,720 | 9/1980 | Taoka et al. | 435/142 |
| 4,339,536 | 7/1982 | Kato et al. | 435/142 |

OTHER PUBLICATIONS

Fonken et al., "Chemical Oxidations With Microorganisms", Marcel Pekker Inc., NY, (1972), pp. 37-49.
Nippon Mining Co., "Fermentative Production of a Dicarboxylic Acid", Japan, Kokai, Tokkyo, Koho, 81, 11, 796, (7-1979), Chemical Abstracts 95: 5146y.
Duvnjak et al., "Activation of Unsaturated Fatty Acids by a Cell-Free Extract of *Candida Tropicalis* Cultivated on Tetradecane", Nafta, (Zagreb), 22, (11), (1971), pp. 841-845, Chemical Abstracts 76: 123978b.

Primary Examiner—Lionel M. Shapiro
Assistant Examiner—John E. Tarcza
Attorney, Agent, or Firm—Flynn, Thiel, Boutell & Tanis

[57] ABSTRACT

A process for the preparation of an unsaturated dicarboxylic acid which comprises cultivating under aerobic conditions a yeast belonging to *Candida tropicalis* which is capable of producing an unsaturated dicarboxylic acid from an unsaturated fatty acid or its ester, such as *Candida tropicalis* 104-04 strain, in a medium containing an unsaturated fatty acid having 14 to 22 carbon atoms or its ester, to produce an unsaturated dicarboxylic acid having 14 to 22 carbon atoms; or effecting oxidation of said fatty acid or its ester in the presence of microorganisms of said yeast produced in advance by cultivation in an assimilable carbon source to produce an unsaturated dicarboxylic acid having 14 to 22 carbon atoms; and then recovering the thus-produced unsaturated dicarboxylic acid.

5 Claims, No Drawings

MICROBIOLOGICAL PROCESS FOR THE PREPARATION OF UNSATURATED DICARBOXYLIC ACIDS

This invention relates to a process for the preparation of an unsaturated dicarboxylic acid from an unsaturated monocarboxylic fatty acid or ester thereof, by the use of a yeast.

Unsaturated dicarboxylic acids having a small number of carbon atoms, such as maleic acid and fumaric acid, are employed in a variety of industrial uses. In contrast, there is not known an advantageous process for the preparation of unsaturated dicarboxylic acids having long carbon chains. For this reason, unsaturated dicarboxylic acids having long carbon chains are very expensive and have almost no important commercial uses. However, these long-chained unsaturated dicarboxylic acids are considered to be employable as starting materials for the preparations of a variety of compounds, such as esters, amides, polymers, macrocyclic compounds and addition compounds. Therefore, if an advantageous preparation process were discovered, unsaturated dicarboxylic acids having long carbon chains could be employed in practice in a variety of industrial uses, such as for starting materials for the preparations of plastic materials, coating materials, perfumes, and the like.

As a process for the preparation of a dicarboxylic acid, there is primarily known an oxidation process involving an oxidation reaction of a starting compound that undergoes an oxidation reaction to produce a compound having carboxyl groups, such as a starting compound having primary alcohol groups. However, such an oxidation process is not appropriately applicable to the preparation of an unsaturated dicarboxylic acid because a compound having unsaturated bonds is likely to undergo oxidation and cleavage at the site(s) of the unsaturated bond(s).

As a process for the preparation of a dicarboxylic acid, there is also known a process involving oxidative fermentation using yeast. For instance, Japanese Patent Publication No. 50(1975)-19630 discloses that oxidative fermentation can be used to convert a saturated or unsaturated, hydrocarbon, alcohol, aldehyde or monocarboxylic acid having 12 to 18 carbon atoms into a saturated dicarboxylic acid. In the publication there are disclosed examples using unsaturated compounds, such as hexadecene-1, as the starting compound. However, when an unsaturated starting compound is used, the oxidation reaction is reported to give, as a principal product, a saturated dicarboxylic acid having a reduced number of carbon atoms. Other products obtained also are dicarboxylic acids of the saturated type. Accordingly, it is understood that the number of unsaturated bonds present is diminished by sidereactions, such as oxidation and cleavage.

All of the known processes for the preparation of dicarboxylic acids by means of yeast, including processes other than those mentioned above, give saturated dicarboxylic acids. Thus, no process is known for the preparation of an unsaturated dicarboxylic acid in which the position of the unsaturated bonds and the stereostructure of the starting compound are transferred, without change, into the resulting dicarboxylic acid.

Upon study of strains belonging to the species of *Candida tropicalis* capable of producing dicarboxylic acids from saturated fatty acid esters, for the purpose of determining the actions of these strains on unsaturated fatty acids and their esters, the present inventors discovered strains that are capable of producing an unsaturated dicarboxylic acid from an unsaturated monocarboxylic fatty acid or its ester, which unsaturated dicarboxylic acid product has the same number of carbon atoms as the fatty acid group of the starting compound, and in which the position of the unsaturated bonds and the stereostructure of the starting compound are maintained. Accordingly, the invention provides a process for the preparation of an unsaturated dicarboxylic acid utilizing the characteristic action of the special strains of the species of *Candida tropicalis*.

The present invention provides a process for the preparation of an unsaturated dicarboxylic acid which comprises cultivating, under aerobic conditions, a yeast belonging to the species of *Candida topicalis*, which yeast is capable of producing an unsaturated dicarboxylic acid from an unsaturated monocarboxylic fatty acid or its ester, in a medium containing an unsaturated monocarboxylic fatty acid having 14 to 22 carbon atoms or ester thereof, in order to produce an unsaturated dicarboxylic acid having 14 to 22 carbon atoms; or oxidizing said unsaturated monocarboxylic fatty acid having 14 to 22 carbon atoms or its ester, in the presence of microorganisms of said yeast produced in advance by cultivation in an assimilable carbon source, to produce an unsaturated dicarboxylic acid having 14 to 22 carbon atoms, and recovering the unsaturated dicarboxylic acid produced thereby.

According to the invention, an unsaturated dicarboxylic acid having 14 to 22 carbon atoms can be advantageously obtained, on an industrial scale, starting from an easily available source.

The invention is further described hereinbelow.

The yeast employed in the invention belongs to the species of *Candida tropicalis* and it has activity for producing an unsaturated dicarboxylic acid from an unsaturated monocarboxylic fatty acid or its ester. An example of the yeast includes *Candida tropicalis* 104-04, which was deposited, on Sept. 24, 1980, at the Fermentation Research Institute, The Agency of Industrial Science and Technology, located at 1-1-3, Higashi-Yatabe-machi, Ibaraki Prefecture, Japan, and has been added to its permanent collection of microorganisms, under the deposition number FERM-P No. 5713. This deposition was transferred to FERM BP-49 on May 1, 1981 by the Fermentation Research Institute.

The microbiological characteristics of the above-mentioned strain are as follows:

Fermentability of saccharide:
  glucose (+); lactose (−); melibiose (−); saccharose (+); galactose (+); maltose (+); raffinose (−)

Assimilability of saccharide:
  glucose (+); galactose (+); maltose (+); lactose (−); sorbitol (+); xylose (+); arabinose (−); raffinose (−); mannitol (+)

Assimilability of ethanol: (+)

Gelatin liquification ability: (−)

Vitamin requirement: biotin

Assimilability of potassium nitrate: (−)

Decomposability of arbutin: (+)

The carbon source, that can be employed as the starting material for the preparation of an unsaturated dicarboxylic acid, is an unsaturated monocarboxylic fatty acid having 14 to 22 carbon atoms or esters thereof. A single compound or a mixture of such compounds can be employed as the carbon source.

The unsaturated monocarboxylic fatty acid having 14 to 22 carbon atoms can have a straight chain or a branched chain. The unsaturated fatty acid can be a natural one, such as one that is obtained from plants and animals, or it can be a synthetically produced one. Moreover, there is no limitation on the position and number of the unsaturated bonds in the molecule. In view of the availability and industrial uses of the product, unsaturated monocarboxylic fatty acids having unsaturated bonds at the terminals are not suitable in the invention. As the above-mentioned unsaturated fatty acids, acids such as myristoleic acid, 2-hexadecenoic acid, palmitoleic acid, oleic acid, elaidic acid, linoleic acid, linolenic acid and erucic acid, are preferred. It is preferred that said unsaturated monocarboxylic fatty acid has the formula: $CH_3-R-COOH$, wherein R is a divalent aliphatic hydrocarbon group containing from 12 to 20 carbon atoms and having from 1 to 4 double bonds, especially from 1 to 3 double bonds.

The unsaturated monocarboxylic fatty acids, such as those listed above, give as principal products, the corresponding unsaturated dicarboxylic acids in which the terminal methyl groups are converted into carboxyl groups, such as 5-tetradecenedioic acid, 2-hexadecenedioic acid, 7-hexadecenedioic acid, 9-cis-octadecenedioic acid, 9-trans-octadecenedioic acid, 6,9-octadecadienedioic acid, 3,6,9-octadecatrienedioic acid and 5-docosenedioic acid, respectively, by use of the process of the invention.

In place of the unsaturated monocarboxylic fatty acids there can be employed, as the starting compound, esters of the above-mentioned unsaturated fatty acids with an alcohol. The alcohol preferably is one having 1 to 4 carbon atoms. Examples of the preferred alcohols include primary alcohols such as methyl alcohol, ethyl alcohol, n-propyl alcohol and n-butyl alcohol, and secondary alcohols such as isopropyl alcohol. Also, glycerol esters of the unsaturated monocarboxylic fatty acids can be employed as the starting compounds.

These unsaturated monocarboxylic fatty acid esters give, as the principal products, the corresponding unsaturated dicarboxylic acids having groups corresponding to the unsaturated fatty acid skeleton, regardless of the alcohol residue. In other words, an unsaturated dicarboxylic acid is produced having carboxyl groups converted from the terminal methyl and ester groups of the starting compound.

According to the invention, the unsaturated monocarboxylic fatty acid or its ester is employed as the carbon source for the cultivation of the aforementioned microorganism, under aerobic conditions, to produce an unsaturated dicarboxylic acid having 14 to 22 carbon atoms. Alternatively, the microorganism can be initially cultivated in a medium containing a different carbon source assimilable by the microorganism, rather than the above-mentioned unsaturated fatty acid, such as acetic acid, citric acid, succinic acid, glucose, sorbitol or n-paraffin. The unsaturated monocarboxylic fatty acid is then added to the medium when the microorganism has grown sufficiently, and cultivation is continued, under aerobic conditions, to produce the unsaturated dicarboxylic acid.

In the alternative, resting cells of the aforementioned microorganism can be employed for the preparation of the unsaturated dicarboxylic acid in the following manner. First, the microorganism is cultivated in a medium containing a carbon source assimilable by the microorganism and different than the above-mentioned unsaturated monocarboxylic fatty acid, i.e., the starting compound, as listed above. Subsequently, the thus-cultivated microorganism is removed and employed for the enzymatic oxidation of the unsaturated fatty acid or its ester to obtain the unsaturated dicarboxylic acid. This reaction can be carried out by suspending the microorganism, after it has been removed from the cultivated mixture and washed with a physiological saline solution, in a conventional buffer solution, such as phosphate buffer solution (pH 7.5). This suspension is shaken in a thermostatic shaker after addition of an appropriate amount of the unsaturated fatty acid or its ester. In the process where the resting cells of the microorganism are used, the cultivation step of the microorganism and the oxidation step can be conducted separately. In the oxidation step, the microorganism can no longer be cultivated because of no carbon source and the starting material to be employed in the oxidation step, the unsaturated monocarboxylic acid or ester thereof, is not used for cultivation of the microorganism.

The carbon source is preferably maintained in contact with the aqueous phase and the microorganism. In most cases, vigorous stirring or shaking is generally satisfactory, because most of the unsaturated fatty acids and their esters are liquid. If desired, sufficient contact can be accomplished by addition of a surface active agent or the like.

The cultivation process of the invention is carried out in a medium containing the aforementioned carbon source and other conventional nutrients, such as a nitrogen source and an inorganic salt. Examples of suitable nitrogen sources include organic and inorganic nitrogen-containing compounds, such as peptone, urea, ammonium phosphate, ammonium chloride, ammonium sulfate and ammonium nitrate. Examples of the inorganic salts include phosphates, sulfates and hydrochlorides of sodium, potassium, magnesium, iron, nickel and zinc, such as $KH_2PO_4$, $K_2HPO_4$, $Na_2HPO_4.12H_2O$, $MgSO_4.7H_2O$, $FeSO_4.7H_2O$, $ZnSO_4.7H_2O$, $NiCl_2.6H_2O$ and NaCl. Moreover, other nutrients, such as yeast extract, corn steep liquor, meat extract and D-biotin, can be added to the medium for assisting the growth of the yeast.

The kinds and amounts of these additives can be determined properly according to the general technical knowledge in the art for the cultivation of microorganisms.

The cultivation is carried out at room temperature or at a temperature slightly higher than room temperature. A temperature in the range of 20° to 40° C. is preferred. The cultivation medium is properly adjusted to pH 5.5-8.5. Since the pH value of the cultivation medium is apt to decrease as the cultivation advances, the pH is preferably adjusted by addition of a neutralizing agent, such as ammonia, sodium hydroxide or potassium hydroxide.

The cultivation is, moreover, carried out under aerobic conditions such as with shaking or stirring under aeration. These procedures can bring about satisfactory contact between the unsaturated monocarboxylic fatty acid used as the starting compound, the liquid culture medium and the air phase.

In the cultivation described above, the microorganism is grown in order to oxidize the unsaturated monocarboxylic fatty acid or its ester so that an unsaturated dicarboxylic acid accumulates in the culture medium.

When D-biotin is introduced as a nutrient, and the unsaturated fatty acid or its ester is introduced in the medium together with another carbon source, such as acetic acid, glucose, sorbitol, citric acid or succinic acid, the microorganism grows initially on the carbon source rather than on the unsaturated monocarboxylic fatty acid or its ester. The thus-grown microorganism then begins oxidation of the unsaturated momocarboxylic fatty acid or its ester.

The unsaturated dicarboxylic acid produced and accumulated in the medium can be recovered and isolated in a known manner. For instance, extraction with an organic solvent or precipitation by adjustment of the pH value of the liquid culture medium are generally employed. More specifically, the liquid culture medium can be, if necessary, treated by an appropriate method, such as centrifuging or filtration, to remove the remaining substrate and microorganism. The thus-treated liquid culture medium is then subjected to an appropriate procedure, such as extraction with diethyl ether, or the like, after acidification or selective adsorption-desorption, using an ion exchange resin, so as efficiently to isolate the desired product.

The unsaturated dicarboxylic acid product can be identified as follows. The liquid culture medium or the reaction liquid is made alkaline with potassium hydroxide in order to dissolve the unsaturated dicarboxylic acid. A certain amount of the solution is taken, acidified with concentrated hydrochloric acid and extracted with diethyl ether. The ether extract is then treated with diazomethane to carry out methylation and is then subjected to analysis by gas chromatography and GC—MS (gas chromatography and mass spectrum measurement). The amount of the unsaturated dicarboxylic acid product present is determined in the above-mentioned analytical procedure by means of a working curve prepared in advance based on a standard dicarboxylic acid sample.

As described hereinbefore, the invention thus provides a process for the preparation of unsaturated dicarboxylic acids that at present can be prepared only with difficulty by synthetic methods, wherein a microbiological process is applied to an unsaturated monocarboxylic fatty acid or its ester.

The present invention is now further described more in detail by reference to the following illustrative examples.

EXAMPLE 1

Preparation of octadecenedioic acid from oleic acid using *Candida tropicalis* 104-04 strain In a ribbed flask there were placed 15 ml. of a liquid culture medium (pH 7.0) comprising 20 g. of sorbitol, 1 g. of $KH_2PO_4$, 3 g. of $K_2HPO_4$, 0.2 g. of $MgSO_4.7H_2O$, 12 g. of urea, 10 mg. of $FeSO_4.7H_2O$, 10 mg. of $ZnSO_4.7H_2O$ and 0.1 mg. of D-biotin, in one liter of water which had been treated with an ion exchanger. To the mixture was added 0.3 ml. of oleic acid, and then the resulting mixture was sterilized with steam at 120° C. for 15 min. to prepare a culture medium.

A strain of *Candida tropicalis* 104-04 was preliminarily cultivated in a separate culture medium containing yeast extract, malt extract and glucose. Several drops of this cultivated medium were inoculated on the above-prepared culture medium.

The cultivation was carried out at 30° C. Since the pH value of the culture medium decreased as the microorganism grew, an aqueous sodium hydroxide solution was added to adjust the pH value to 7.0-7.5.

Forty-eight hours after the inoculation the liquid culture medium was subjected to analysis for identification of the unsaturated dicarboxylic acid product. Quantitative analysis was also carried out. The resulting data are set forth in Table 1.

The unsaturated dicarboxylic acid product was extracted from the liquid culture medium with diethyl ether in a conventional manner. Upon removal of the solvent by evaporation, there were obtained 21 mg. of crude crystals. The crystals had a melting point of 69°–70° C. after recrystallization from n-hexane. This melting point is identical to the melting point of 9-cis-octadecenedioic acid given in J. Gensler et al., J. A. C. S., 77, 4846, (1955), namely, mp. 69°–70° C.

Analysis (%): C, 69.8; H, 10.5: and calculated (%): C 69.2; H 10.3.

IR spectrum measurement also identified the crystals obtained above as 9-cis-octadecenedioic acid.

TABLE 1

| Mother Strain of Microorganism Employed | Amount of Octadecenedioic Acid Produced (g./l.) |
|---|---|
| *Candida Tropicalis* 104-04 | 1.66 |

EXAMPLE 2

Preparation of octadenedioic acid from oleic acid ester using *Candida tropicalis* 104-04 strain The procedures described in Example 1 were repeated, except that the oleic acid was replaced with methyl oleate, ethyl oleate, butyl oleate and triolein (glycerol ester).

Forty-eight hours after the inoculation, the liquid culture medium was subjected to analysis for identification of the unsaturated dicarboxylic acid product in the same manner as described in Example 1. Quantitative analysis was also carried out. The resulting data are set forth in Table 2.

TABLE 2

| Ester Substrate | Amount of Octadecenedioic Acid Produced (g./l.) |
|---|---|
| Methyl oleate | 0.99 |
| Ethyl oleate | 1.50 |
| Butyl oleate | 1.62 |
| Triolein | 0.65 |

EXAMPLE 3

Preparation of dicarboxylic acids from unsaturated monocarboxylic fatty acids and their esters using *Candida tropicalis* 104-04 strain The procedures described in Example 1 were repeated, except that the oleic acid was replaced with elaidic acid, methyl elaidate, 2-hexadecenoic acid, linoleic acid, methyl linoleate, erucic acid and methyl erucate.

Forty-eight hours after the inoculation, the liquid culture medium was subjected to analysis for identification of the unsaturated dicarboxylic acid product, in the same manner as described in Example 1. Quantitative analysis was also carried out. The resulting data are set forth in Table 3.

TABLE 3

| Unsaturated Fatty Acid and Ester | Unsaturated Dicarboxylic Acid Product | Amount (g./l.) |
| --- | --- | --- |
| Elaidic acid | 9-trans-octadecenedioic acid | 1.05 |
| Methyl elaidate | Same | 1.75 |
| 2-Hexadecenoic acid | 2-hexadecenedioic acid | 1.74 |
| Linoleic acid | 6,9-octadecadienedioic acid | 1.47 |
| Methyl linoleate | Same | 0.20 |
| Erucic acid | 5-docosenedioic acid | 1.96 |
| Methyl erucate | Same | 0.50 |

EXAMPLE 4

Preparation of 9-cis-octadecenedioic acid from oleic acid and butyl oleate using stabilized microorganism of *Candida tropicalis* 104-04 strain The same medium as employed in Example 1 was used except that 0.5% of n-hexadecane was added in place of the oleic acid and was used for cultivating the *Candida tropicalis* 104-04 strain at 30° C. for 24 hours. The microorganisms were then separated by centrifuging, washed twice with physiological saline solution, and suspended in 15 ml. of phosphate buffer solution (pH 7.5, 0.5 mole concentration). To the suspension was added 0.3 ml. of oleic acid or butyl oleate, and the mixture was shaken at 30° C. for 24 hours. The mixture was then subjected to analysis for identification of the unsaturated dicarboxylic acid product in the manner as described in Example 1. Quantitative analysis was also carried out. The resulting data are set forth in Table 4.

TABLE 4

| Unsaturated Fatty Acid and Its Ester | Amount of 9-cis-Octadecenedioic Acid Produced (g./l.) |
| --- | --- |
| Oleic acid | 0.10 |
| Butyl oleate | 0.15 |

The embodiments of the invention in which an exclusive property or privilege is claimed are defined as follows:

1. A process for producing a long-chain, unsaturated, dicarboxylic acid, which comprises: culturing, under aerobic conditions, the strain *Candida tropicalis* FERM BP-49 capable of converting an unsaturated monocarboxylic acid having (1) 14 to 22 carbon atoms, (2) a carboxyl group at one terminal thereof and (3) a methyl group at the other terminal thereof, or ester thereof, to the corresponding unsaturated dicarboxylic acid having (1) carboxyl groups at both terminals thereof, (2) the same number of total carbon atoms, (3) the same number and position of unsaturated carbon atoms, and (4) the same stereostructure as said unsaturated monocarboxylic acid, in a nutrient medium containing said unsaturated monocarboxylic acid or ester thereof, until said corresponding unsaturated dicarboxylic acid is produced; and then recovering said corresponding unsaturated dicarboxylic acid.

2. A process as claimed in claim 1, in which said unsaturated monocarboxylic acid is myristoleic acid, 2-hexadecenoic acid, palmitoleic acid, oleic acid, elaidic acid, linoleic acid, linolenic acid or erucic acid, and the corresponding unsaturated dicarboxylic acid produced is 5-tetradecenedioic acid, 2-hexadecenedioic acid, 7-hexadecenedioic acid, 9-cis-octadecenedioic acid, 9-trans-octadecenedioic acid, 6,9-octadecadienedioic acid, 3,6,9-octadecatrienedioic acid or 5-docosenedioic acid, respectively.

3. A process for producing a long-chain, unsaturated, dicarboxylic acid, which comprises: growing, in a nutrient medium, the strain *Candida tropicalis* FERM BP-49 capable of converting an unsaturated monocarboxylic acid having (1) 14 to 22 carbon atoms, (2) a carboxyl group at one terminal thereof, and (3) a methyl group at the other terminal thereof, or ester thereof, to the corresponding unsaturated dicarboxylic acid having (1) carboxyl groups at both terminals thereof, (2) the same number of total carbon atoms, (3) the same number and position of unsaturated carbon atoms, and (4) the same stereostructure as said unsaturated monocarboxylic acid; separating the cell mass comprising said strain from the nutrient medium; and contacting said cell mass, under aerobic conditions, with said unsaturated monocarboxylic acid, or ester thereof, to effect enzymatic oxidation of said unsaturated monocarboxylic acid until said corresponding unsaturated dicarboxylic acid is produced; and then recovering said corresponding unsaturated dicarboxylic acid.

4. A process as claimed in claim 3, in which said unsaturated monocarboxylic acid is myristoleic acid, 2-hexadecenoic acid, palmitoleic acid, oleic acid, elaidic acid, linoleic acid, linolenic acid or erucic acid, and the corresponding unsaturated dicarboxylic acid produced is 5-tetradecenedioic acid, 2-hexadecenedioic acid, 7-hexadecenedioic acid, 9-cis-octadecenedioic acid, 9-trans-octadecenedioic acid, 6,9-octadecadienedioic acid, 3,6,9-octadecatrienedioic acid or 5-docosenedioic acid, respectively.

5. A process as claimed in claim 1 or claim 3 in which said unsaturated monocarboxylic acid has the formula $$CH_3-R-COOH$$

wherein R is a divalent aliphatic hydrocarbon group containing from 12 to 20 carbon atoms and having from 1 to 4 double bonds, and said unsaturated dicarboxylic acid has the formula $$HOOC-R-COOH.$$

* * * * *